United States Patent [19]

DiSabito et al.

[11] Patent Number: 5,279,308
[45] Date of Patent: Jan. 18, 1994

[54] INTRAUTERINE PRESSURE CATHETER SYSTEM

[75] Inventors: David M. DiSabito, Clarence; George R. Allen, Grand Island, both of N.Y.; James R. Hubbard, Lumberton, N.J.; Joseph C. Naphy, Pennsauken, N.J.; Glenn A. Thomas, N. East Amherst, N.Y.

[73] Assignee: Graphic Controls Corporation, Buffalo, N.Y.

[21] Appl. No.: 19,862

[22] Filed: Feb. 19, 1993

[51] Int. Cl.$^5$ .............................................. A61B 5/103
[52] U.S. Cl. ..................................... 128/775; 128/748
[58] Field of Search ....................... 128/675, 748, 775; 73/715

[56] References Cited

U.S. PATENT DOCUMENTS

| | | | |
|---|---|---|---|
| 4,722,348 | 2/1988 | Ligtenberg et al. | 128/675 |
| 4,873,986 | 10/1989 | Wallace | 128/670 |
| 4,901,735 | 2/1990 | von Berg | 128/748 |
| 4,944,307 | 7/1990 | Hon et al. | 128/748 |
| 4,960,127 | 10/1990 | Noce et al. | 128/675 |
| 4,966,161 | 10/1990 | Wallace et al. | 128/748 |
| 5,000,049 | 3/1991 | Cooper et al. | 73/730 |
| 5,025,787 | 6/1991 | Sutherland et al. | 128/642 |
| 5,048,531 | 9/1991 | Spotts et al. | 128/675 |
| 5,067,491 | 11/1991 | Taylor, II et al. | 128/748 |
| 5,085,223 | 2/1992 | Lars et al. | 128/675 |
| 5,105,820 | 4/1992 | Moriuchi et al. | 128/675 |

*Primary Examiner*—Max Hindenburg
*Attorney, Agent, or Firm*—Ratner & Prestia

[57] ABSTRACT

An intrauterine pressure catheter system for monitoring pressure in the uterus of a mother during labor and delivery. The system includes a reusable junction box with a needle communicating directly to a pressure transducer sensor. The sensor transmits changes in pressure to a conventional pressure monitor. A connector attached to the catheter is pushed into the junction box and is held in place by a plastic latch. Inside this connector are an elastomeric plug and an adjacent diaphragm. When the connector is installed in the junction box, the needle pierces the plug and the tip enters the air-filled volume between the plug and the diaphragm. Fluid pressure in the catheter is communicated to the diaphragm surface and, in turn, passed to the air in the volume between the diaphragm and the plug. Thus, the intrauterine pressure is transmitted directly to the sensor. The system may be zeroed to atmosphere by simply removing the connector from the junction box.

18 Claims, 9 Drawing Sheets

INTRAUTERINE PRESSURE CATHETER SYSTEM

FIELD OF THE INVENTION

The present invention relates generally to a catheter system capable of monitoring changes in intrauterine pressure during labor and delivery. More specifically, the present invention relates to a system which combines a disposable catheter which can be latched, through a disposable connector, to a junction box containing a pressure sensor. The junction box and relatively expensive pressure sensor are reusable.

BACKGROUND OF THE INVENTION

The development of devices used to monitor intrauterine pressure in labor and delivery has vastly improved the ability of a physician to assess the health of both fetus and mother during childbirth. The use of such a device, often in conjunction with a fetal heart monitor, serves to warn a physician of potential problems before they become life-threatening. For example, an intrauterine pressure monitor allows a physician to assess whether adequate oxygen and nutrients are being transferred from mother to fetus and whether the rate, duration, and intensity of the intrauterine contractions are acceptable.

Two types of devices are commonly used to monitor intrauterine pressure in a mother during labor and delivery. Often an external device secured to the mother's abdomen is used. For example, a pressure sensitive button, called a tocotransducer, capable of measuring the frequency and duration of intrauterine contractions is available. This type of external device has the advantage of being completely noninvasive. Therefore, it eliminates any threat of infection and risks little discomfort to the mother.

External devices frequently provide inaccurate measurements of intrauterine pressure, however, because they are sensitive to excessive movement and to obesity of the mother. In addition, external devices are poorly capable of measuring the actual intensity of intrauterine contractions. For these reasons, an external device is ineffective in many childbirth situations, specifically, when there is risk of complication and the physician desires very accurate information.

Devices capable of measuring intrauterine pressure when inserted into the uterus provide a more accurate measure of events during labor than the external devices and, in particular, a more accurate measure of intrauterine contraction intensity. Because the nature and duration of the contraction is measured directly, the intrauterine devices minimize the potential for inaccurate readings due to the mother's movement or obesity.

Historically, the most common intrauterine devices are those which use a liquid-filled catheter which, after it is inserted into the uterus of the mother, is hydraulically connected to an external pressure transducer. The pressure transducer is typically mounted to a bedside IV stand and is connected to a monitor device. The monitor may be a cathode ray tube display, a digital display and recording device, a printer, or a plotter.

Typically, the catheter is primed with a sterile solution to provide a continuous column of liquid from the pressure transducer to the tip of the catheter within the uterus. Upon contraction of the uterus, the increased intrauterine pressure causes displacement of the liquid in the catheter which is subsequently measured by the pressure sensor and transmitted to the monitor. The monitor displays the mother's intrauterine pressure as a function of time.

The pressure transducer may be used with a disposable dome which fits over the transducer diaphragm. Typically, there are two ports in the dome, a side port which is connected to the liquid-filled catheter after it is primed with a sterile solution, and a second port which is used for calibration and zero balancing.

There are two significant disadvantages of this type of intrauterine device. First, cumbersome manipulations and time are required to fill and prime the catheter with sterile solution. Second, air bubbles frequently enter the open end of the catheter. Such air bubbles require flushing of the catheter with a sterile solution or replacement of the entire catheter, either of which may cause discomfort to the mother.

An improved, in-dwelling, catheter apparatus useful for monitoring changes in intrauterine pressure during labor is described in U.S. Pat. No. 4,966,161 issued to Wallace et al. The catheter has apertures near its distal end, placing a first chamber formed in the distal catheter tip in fluid communication with the fluid of the uterus. Liquids enter the first chamber and form a liquid column with a liquid-air interface. A second chamber, filled with air, is defined by an interior lumen extending the length of the catheter up to the first chamber. An air column is formed by air trapped in the second chamber. The relative volumetric capacity of the first and second chamber is such that, under maximum uterine pressures, the trapped air column will limit the liquid column in the first chamber, minimize hydrostatic pressure error, and prevent fluid from entering the second chamber. Uterine pressure is transmitted from the partially liquid-filled first chamber, through the air-filled column of the second chamber, to the diaphragm of the pressure transducer—which is also part of the catheter.

The design of the '161 device eliminates the requirement for the cumbersome flushing and filling of the catheter found in previous designs. That device requires, however, that the volumes of the two chambers be carefully controlled. Moreover, the pressure sensor is mounted in the catheter and is in direct contact with the intrauterine fluid. Therefore, the entire catheter and pressure sensor device must be discarded after use to prevent transmitting infectious agents from one patient to another. This presents a significant economic disadvantage; the pressure sensor is one of the most costly components of the device.

U.S. Pat. No. 5,000,049 issued to Cooper et al. discloses a diaphragm-type pressure gauge for use with medical apparatus such as catheters. The gauge has a pressure diaphragm which responds to a change in fluid pressure and activates a mechanical pressure signal translation mechanism. A second, sealing diaphragm may be disposed adjacent the first diaphragm to transmit pressure changes thereto without allowing the passage of materials between the two diaphragms. (Alternatively, the pressure diaphragm may be sealed with a biocompatible material.) The fluid may be provided by a catheter whose wall is disposed against the pressure diaphragm so that the diaphragm senses fluid pressure changes without contact between the diaphragm and the fluid. The gauge is essentially reusable because the pressure diaphragm does not contact the fluid.

The design of the '049 device incorporates a relatively complex method of connecting the gauge and transducer to the measuring circuit, involving, in the preferred embodiment, two diaphragms (one in the wall of a tube). Moreover, the design does not focus on the catheter and, consequently, fails to provide a lumen in the catheter for adding fluid to and removing fluid from the body. Finally, the '049 design risks significant attenuation of the pressure signal because it uses a mechanical pressure signal translation mechanism and the catheter wall to transmit the pressure signal.

U.S. Pat. No. 4,944,307 issued to Hon et al. discloses an intrauterine catheter which is connected at one end, through an adapter, to the input of a pressure transducer and closed at its uterine end by a flexible membrane. The catheter is filled with a sterile fluid. No air is in either the catheter or pressure transducer. A change in intrauterine pressure is transmitted to the pressure transducer without contact between the intrauterine fluid and the pressure transducer.

Although the pressure measuring system of the '307 patent can be zeroed while the catheter is in the uterus, the procedure required is relatively complex. Also relatively complex is the procedure required to set up and insert the system in the uterus. The catheter may be filled with a silicone-based fluid, which could enter the uterus upon development of a leak in the tip membrane. Finally, the design of the '307 device fails to provide a lumen in the catheter for adding fluid to and removing fluid from the body.

U.S. Pat. No. 5,105,820 issue to Moriuchi et al. discloses a disposable pressure transducer for measuring fluid pressure which includes a sensor assembly in a housing. The housing has a fluid chamber and a chamber accomodating the sensor assembly; the two chambers are integrally formed. Pressure changes are transferred to the fluid chamber and then to a diaphragm of a pressure sensor through a pressure-transmitting medium disposed between the two chambers. The pressure-transmitting medium thus isolates the sensor from the fluid whose pressure is being measured.

The apparatus of the '820 reference is costly because the sensor is disposable. Like the pressure measuring system of the '307 patent, there is no structure disclosed in the disposable pressure transducer apparatus of the '820 patent to zero the apparatus instantaneously. Finally, the design of the '820 device fails to provide a lumen in the catheter for adding fluid to and removing fluid from the body.

To overcome the shortcomings of the prior art, a new intrauterine pressure catheter system is provided. The general object of the present invention is to provide a system capable of monitoring intrauterine pressure in a woman during labor and delivery which is economical to use and reuse. In order to achieve that general object, a more specific object is to provide an intrauterine pressure catheter system in which all of the components which come into contact with the mother's bodily fluids and tissues are sterilizable, inexpensive, and disposable. Related objects are to separate the expensive pressure sensor from the disposable part of the system and to isolate the pressure sensor from the mother so that it can be reused without risk of transferring infectious agents from one patient to another.

Further objects are to provide a system which is safe to both the mother and the physician. Its use must create minimal discomfort to the mother and provide accurate information to the physician. In addition, the use of the system must avoid the complexity of running a liquid-filled tube from the catheter to a stand-mounted transducer.

Still another object of the present invention is to provide a system in which the transducer can be zeroed after the catheter has been inserted into the uterus and the appropriate monitoring device connected to the transducer. Yet another object is to provide an intrauterine pressure catheter system which allows fluid samples to be withdrawn from, and fluids to be infused into, the uterus.

SUMMARY OF THE INVENTION

To achieve these and other objects, and in view of its purposes, the present invention provides an intrauterine pressure catheter system including a reusable junction box with a needle communicating directly to a pressure transducer sensor. The sensor transmits changes in pressure to a conventional pressure monitor. A connector attached to the catheter is pushed into the junction box and is held in place by a plastic latch. Inside this connector are an elastomeric plug and an adjacent diaphragm. When the connector is installed in the junction box, the needle pierces the plug and the tip enters the air-filled volume between the plug and the diaphragm. Fluid pressure in the intrauterine pressure catheter is communicated to the diaphragm surface and, in turn, passed to the air in the volume between the diaphragm and the plug. Thus, the intrauterine pressure is transmitted directly to the sensor. The system may be zeroed to atmosphere by simply removing the connector from the junction box.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which.

DETAILED DESCRIPTION OF THE INVENTION

Figure 1:
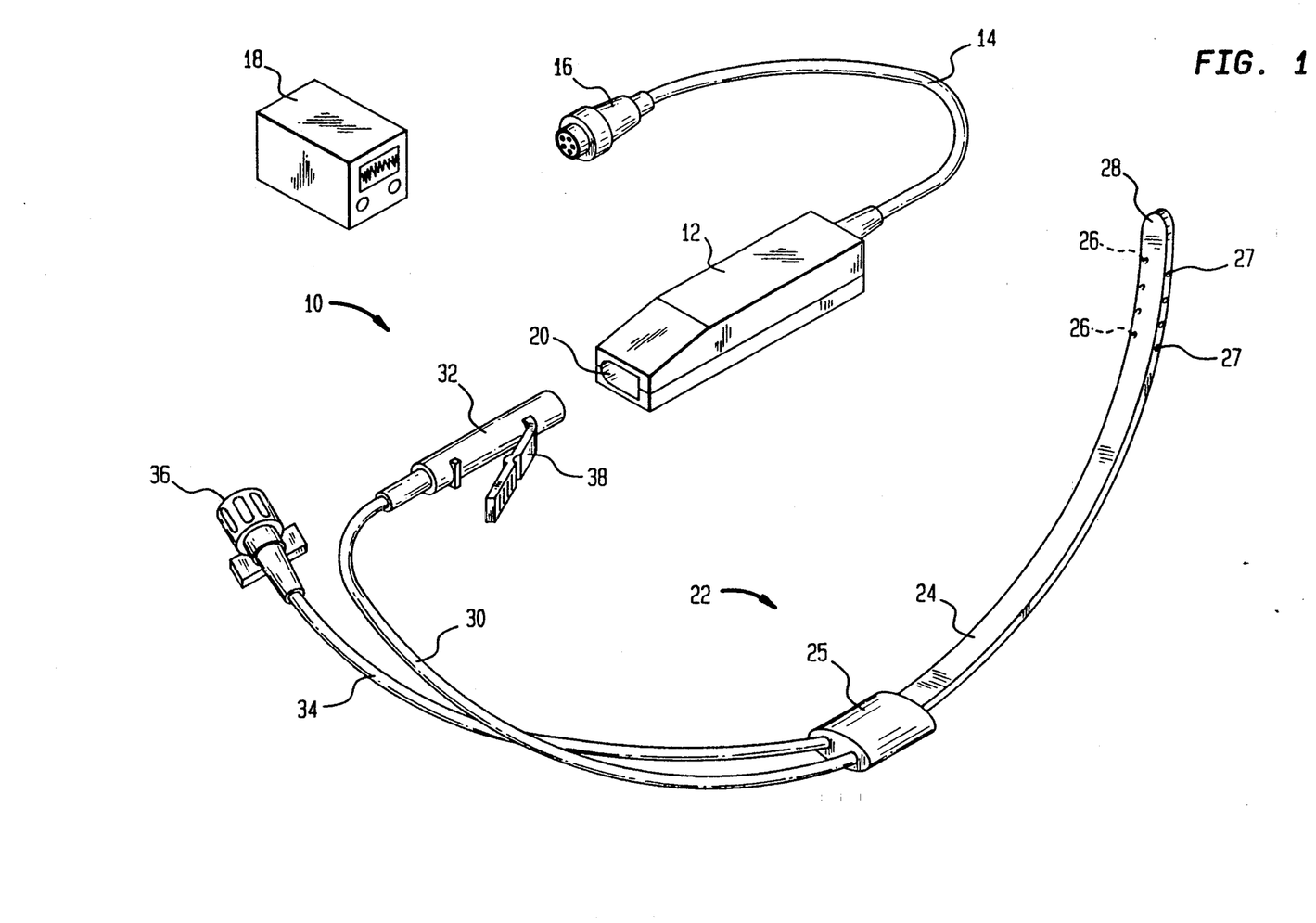
FIG. 1 is an isometric sketch of an intrauterine pressure catheter system according to the present invention.

Referring now to the drawing, wherein like reference numerals refer to like elements throughout, FIG. 1 is an isometric sketch of an intrauterine pressure catheter system 10. System 10 includes a reusable junction box 12 which is connected by a cable 14 to a jack 16. Jack 16 is used to connect junction box 12 to a conventional monitor 18. Junction box 12 is provided with an opening 20.

System 10 also includes a disposable catheter 22. Catheter 22 has a body 24 which is comfortable when inserted into the uterus and alongside the fetus during labor and delivery. Catheter 22 has first apertures 26 in the distal end 28 of body 24 through which fluid may enter or exit catheter 22. Such fluid may travel in tube 34, which runs through sleeve 25 of catheter 22, exits or enters body 24 at first apertures 26, and is connected to a luer 36. Tube 34 may be provided in catheter 22 to inject fluid into the uterus or to sample fluid from the uterus. As part of catheter 22, tube 34 and luer 36 are discarded after use.

Distal end 28 of body 24 of catheter 22 also has second apertures 27 through which fluid may enter or exit catheter 22. Such fluid may travel in lumen 30, which runs inside body 24 of catheter 22, exits body 24 at sleeve 25, and is connected to a connector 32. Although lumen 30 and tube 34 are coextensive in body 24, lumen 30 is completely separate and sealed from tube 34. Also as part of catheter 22, lumen 30 and connector 32 are discarded after use.

Connector 32 is provided with a latch 38. When connector 32 is pushed into opening 20 of junction box 12, latch 38 serves to fix connector 32 inside junction box 12. Thus, latch 38 must be flexible. Connector 32 and latch 38 are preferably formed as an integral, plastic component.

Figure 2:
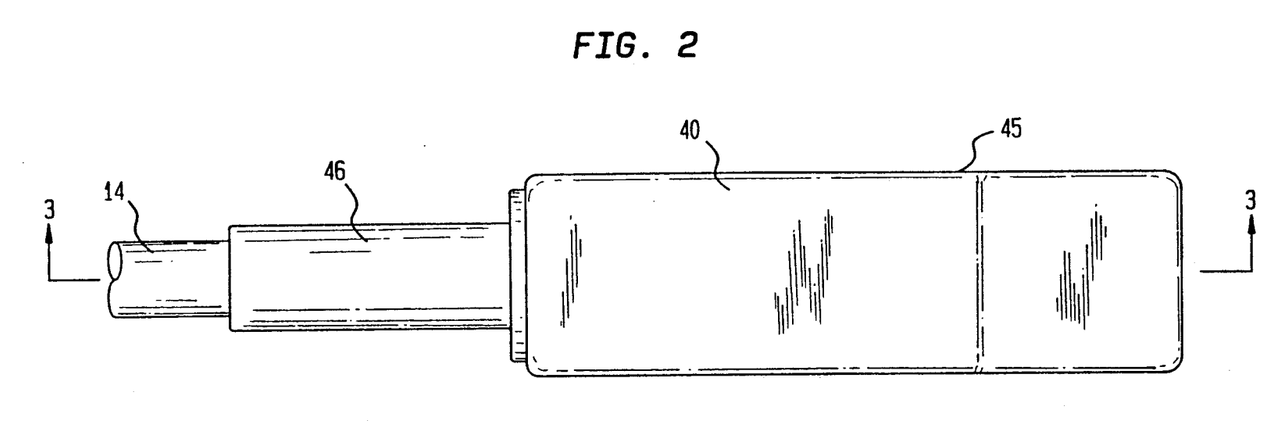
FIG. 2 is a longitudinal view of the junction box of the present invention.
Figure 3:
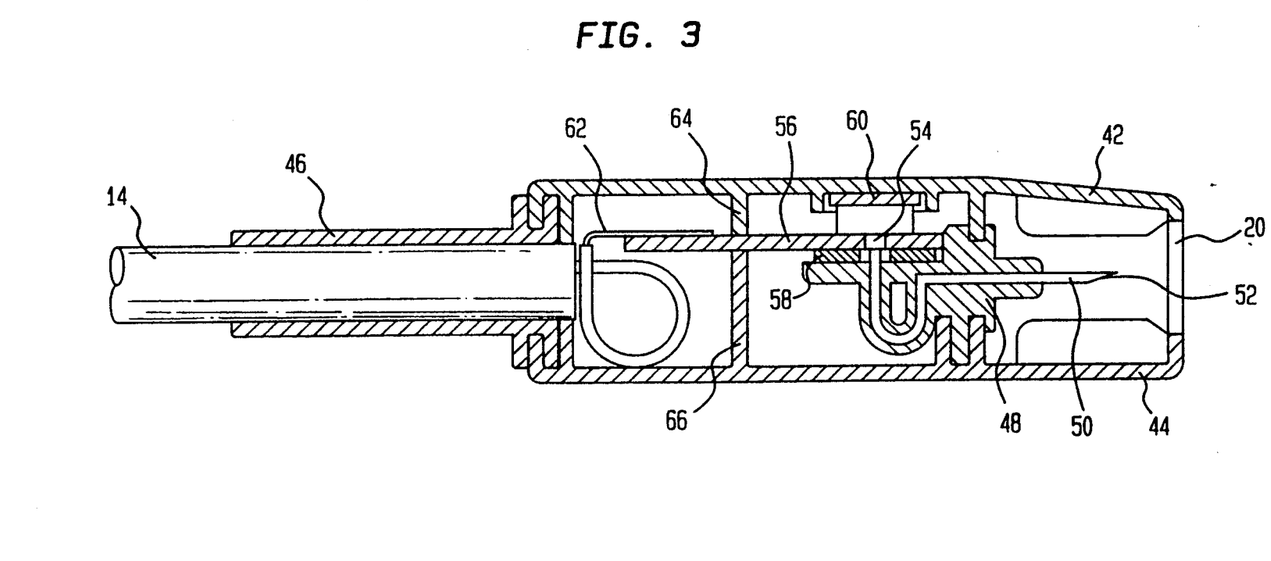
FIG. 3 is a cross-section, taken along the line 3—3 of FIG. 2, of the junction box.

FIG. 2 and FIG. 3 highlight reusable junction box 12 of the present invention. Junction box 12 has a case 40 with an upper half 42 and a lower half 44. Cable 14 enters case 40 at the rear of case 40. A strain relief component 46 is provided to facilitate attachment of cable 14 to case 40 and to assure longevity of that attachment. Strain relief component 46 is preferably affixed to case 40 with an adhesive.

Contained within case 40 of junction box 12 is a needle holder 48 which holds a hollow needle 50 (needle 50 having a bore). Needle holder 48 is preferably affixed to case 40 with an adhesive. The point 52 of needle 50 is positioned so as to pierce a plug (see below) in connector 32 when connector 32 engages junction box 12. Moreover, point 52 is placed well within junction box 12 and opening 20, which receives connector 32, has a relatively small diameter (about 0.3 inches) to protect users from accidental contact. Preferably, point 52 is centered within junction box 12 and located about 0.175 to 0.200 inches from opening 20. The opposite end 54 of needle 50 is in direct communication with the pressure sensor assembly 56.

Sensor 56 is resiliently mounted in junction box 12 between an adhesive-backed foam seal 58, which seals sensor 56 to needle holder 48, and a foam pad 60, which is compressed against upper half 42 of case 40. Thus, sensor 56 is isolated from the impact, vibration, and other mechanical abuse encountered in normal operation. Sensor 56 is electrically connected with leads 62 (e.g., by solder, weld, adhesive, or the like) which carry electrical signals from sensor 56 to cable 14. Two deflection barriers 64 and 66 are placed near the connection of leads 62 to sensor 56 to restrict the movement of sensor 56 during impact and, thus, to resist excessive deflection which would cause sensor 56 to lift from foam seal 58. Sensor 56 converts physical pressure signals into corresponding electrical signals.

Junction box 12 is constructed to provide a complete seal of sensor 56 so that junction box 12 can be immersed in cleaning solution without admitting fluid inside the sensor-mounting region of junction box 12. TO achieve that end, junction box 12 is joined at its perimeter by an adhesive seal 45 which may require a significant time to cure. Junction box 12 also includes a self-aligning feature which includes a series of posts (not shown) on one case half (42, 44) and post holes (not shown) on the other case half (42, 44). These posts and holes are designed to assure a press fit which resists separation when case halves 42 and 44 are forced together. They are positioned to provide sufficiently uniform holding force around the entire perimeter of case 40 to prevent movement between case halves 42 and 44 during adhesive cure.

Turning to FIGS. 4A, 4B, 4C, and 4D, an alternative connector 32 is illustrated as it is attached to junction box 12. Lumen 30 of catheter 22 is housed within the connector latch collar 70 of connector 32 and is attached to junction box 12 by inserting connector latch collar 70 into opening 20 of junction box 12. When connector 32 is fully inserted in junction box 12 in the monitor position shown in FIG. 4D, needle point 52 in junction box 12 pierces the self-sealing, elastomeric (preferably silicone) plug 72 Of connector 32. Plug 72 seals needle 50 in a fluid-tight manner.

Fluid in lumen 30 from catheter 22 is transmitted to the chamber 79. That fluid exerts pressure on the diaphragm 76, causing diaphragm 76 to flex which, in turn, changes the pressure of the air in the volume 78 defined by diaphragm 76 and plug 72. Because needle point 52 is positioned in volume 78 when connector 32 is fully inserted in junction box 12 in the monitor position shown in FIG. 4D, the change in the air pressure in volume 78 is transmitted through needle 50 to sensor 56.

Figure 4A:
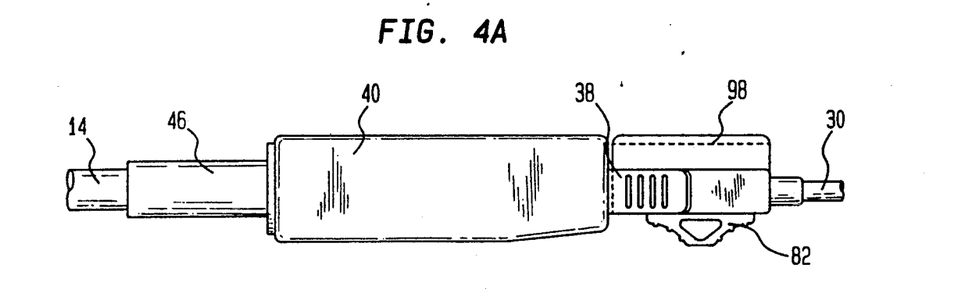
FIGS. 4A, 4B, 4C, and 4D illustrate, in four views (FIG. 4A is a longitudinal view of the connector in the zero position relative to the junction box, FIG. 4B is a cross-section of the longitudinal view shown in FIG. 4A, FIG. 4C is a cross-section taken along the line 4C—4C of FIG. 4B, and FIG. 4D is a cross-sectional view similar to FIG. 4C of the connector in the monitoring position relative to the junction box), the connector of the present invention as attached to the junction box.
Figure 4B:
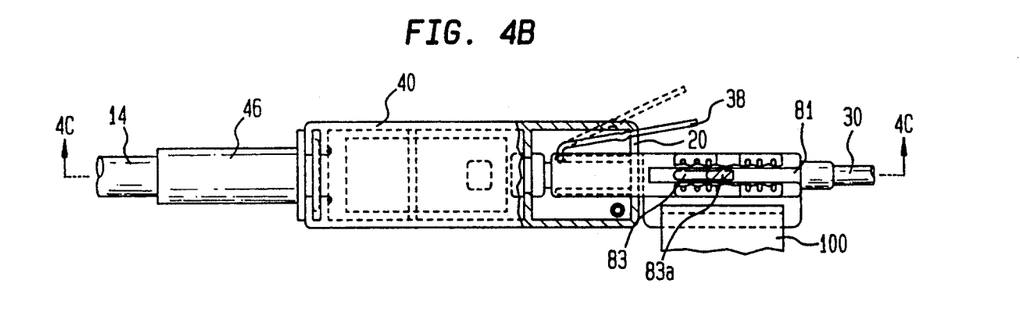

Thus, needle 50 provides direct contact between sensor 56 and volume 78, avoiding the need for a second diaphragm. Needle 50 also allows a relatively simple and reliable pressure connection and helps to assure measurement accuracy. Volume 78 could be filled with liquid rather than air, creating a liquid-liquid pressure interface across diaphragm 76. It is preferred, however, that the bore of needle 50 have a diameter which is sufficiently small that it would produce capillary action if a liquid were placed in needle 50. Consequently, volume 78 is filled with air rather than liquid, creating an air-liquid pressure interface across diaphragm 76. The air and needle 50 assure proper measurement of the pressure signal. Were liquid used in volume 78 and needle 50, the measurement of the pressure signal would be affected by the hydrostatic pressure caused by the capillary action in the needle 50.

Volume 78 is separated and effectively isolated from the fluid-filled chamber 79 of connector 32 by diaphragm 76. Thus, there is no direct air-to-liquid interface. Nor are volume 78 and chamber 79 in direct fluid communication with each other. The isolation of fluid away from volume 78, specifically, and junction box 12, generally, permits junction box 12 to be reused. In contrast, catheter 22 and connector 32 must be discarded after use.

Needle plug 72, a fill plug 74, and diaphragm 76 are mounted in an actuator sleeve 80 of connector 32. Actuator sleeve 80 is affixed to the end of lumen 30 opposite distal end 28 of body 24 of catheter 22. Integrally formed with actuator sleeve 80 is a push button-moved actuator 82. Actuator 82 slides in a track 81 provided in the outside wall of connector latch collar 70. Track 81 has a pair of notches 83, 83A which removably engage actuator 82. Actuator 82 permits system 10 to be zeroed to atmospheric pressure without removing connector 32 from junction box 12.

By sliding actuator 82 from first notch 83, an "on" (monitor) position, to second notch 83A, an "off" (zero) position, needle point 52 in junction box 12 is removed from plug 72, disengaged from volume 78, and exposed to atmospheric pressure. Needle 50 may be exposed to atmospheric pressure through opening 20, which is vented to the atmosphere. Appropriate "on" and "zero" designations and arrows (not shown) may be provided on or adjacent actuator 82 to assist the user. Sensor 56 in junction box 12 is vented through cable 14 and an opening in jack 16 to maintain sensor 56 always at atmospheric pressure, thus avoiding any influence on the measured pressure signal.

Fill plug 74 is self sealing and permits the insertion of a syringe. Suction on the syringe allows liquid (usually saline solution) to be drawn into catheter 22 while air is removed. Thus, catheter 22 can be filled with liquid while leaving a minimum amount of air. A reverse filling process can also be used in which fluid is forced via a syringe into fill plug 74. This filling process can continue until the entire connector 32 and lumen 30 of catheter 22 are full of fluid.

As connector 32 is pushed into engagement with junction box 12, latch 38 is displaced toward connector latch collar 70. Once connector 32 has engaged junction box 12, latch 38 expands away from connector latch collar 70, engages case 40 of junction box 12, and locks connector 32 inside junction box 12. To disengage connector 32 from junction box 12, latch 38 is depressed and connector 32 is pulled out of opening 20 and away from junction box 12.

Figure 5:
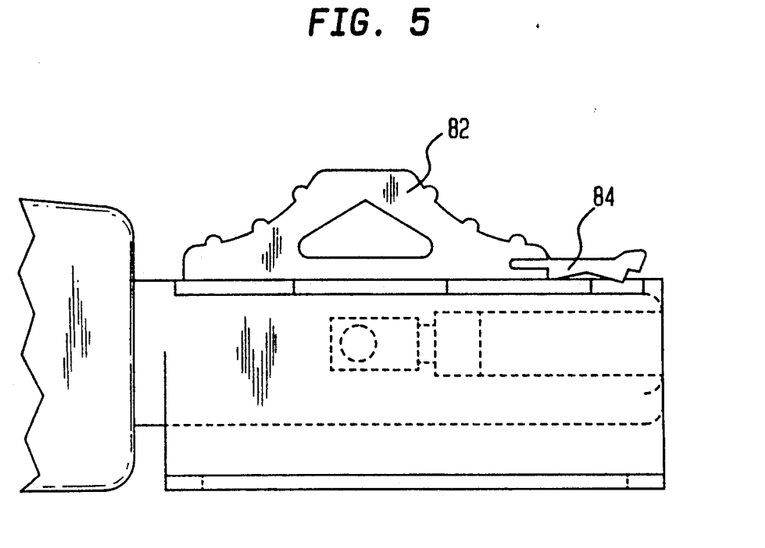
FIG. 5 illustrates the connector containing an anti-return arm.

To prevent unwanted zeroing of sensor 56 through displacement of actuator 82, connector 32 may be provided with an anti-return arm 84 as illustrated in FIG. 5. Arm 84 prevents actuator 82 from being accidentally pulled from the on (monitor) position to the zero position. Arm 84 must be manually released before zeroing is possible. Arm 84 also minimizes the force required to move actuator 82 between notch positions.

Figure 6:
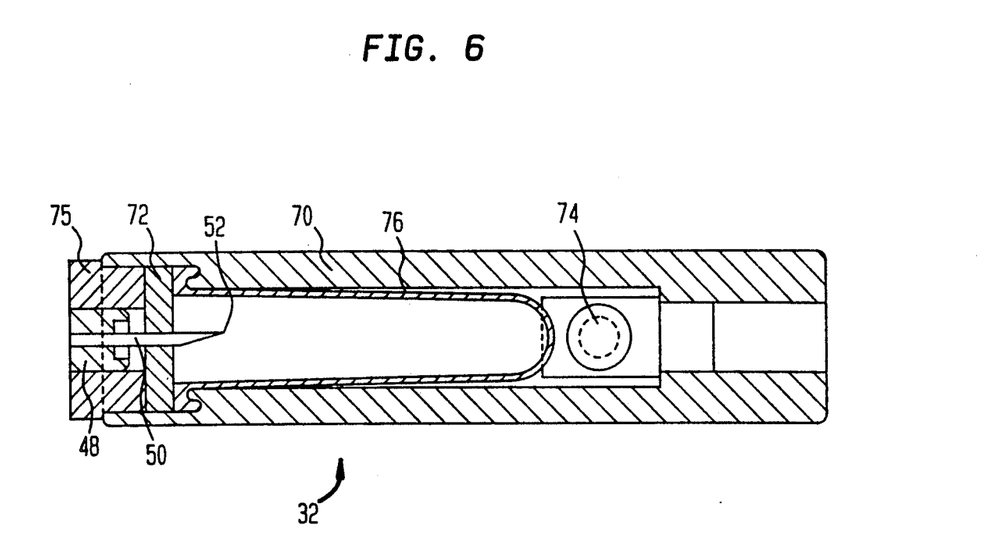
FIG. 6 illustrates a connector without the actuator.

FIG. 6 illustrates a preferred connector 32 in which actuator 82 and actuator sleeve 80 have been eliminated. Needle plug 72, fill plug 74, and diaphragm 76 are mounted in connector latch collar 70. A connector sleeve 75 is ultrasonically joined to connector latch collar 70 and functions to fix needle plug 72 and diaphragm 76 in position in a sealed manner. Pressure sensor 56 (not shown in FIG. 6) can be zeroed to atmospheric pressure by simply removing connector 32 from junction box 12. This design permits enlargement of diaphragm 76, facilitating a more accurate measurement of the change in pressure. Thus, it is currently the preferred design.

The use of a fluid filter instead of diaphragm 76 in connector 32 provides a direct fluid pressure connection between the uterus and sensor 56. Such a filter must not block liquid interchange and should be sufficiently fine to prevent any virus, bacteria, or other contamination from travelling from needle 50 to the uterus.

A hydrophobic filter may also be used in place of diaphragm 76 in connector 32. The hydrophobic filter should also be sufficiently fine to block any virus, bacteria, or other contamination on or in reusable needle 50 from reaching the uterus. In addition, the hydrophobic filter, as with diaphragm 76, should prevent fluid in catheter 22 from entering needle 50 and causing undesirable offset pressures or needle bore contamination or blockage.

Figure 7:
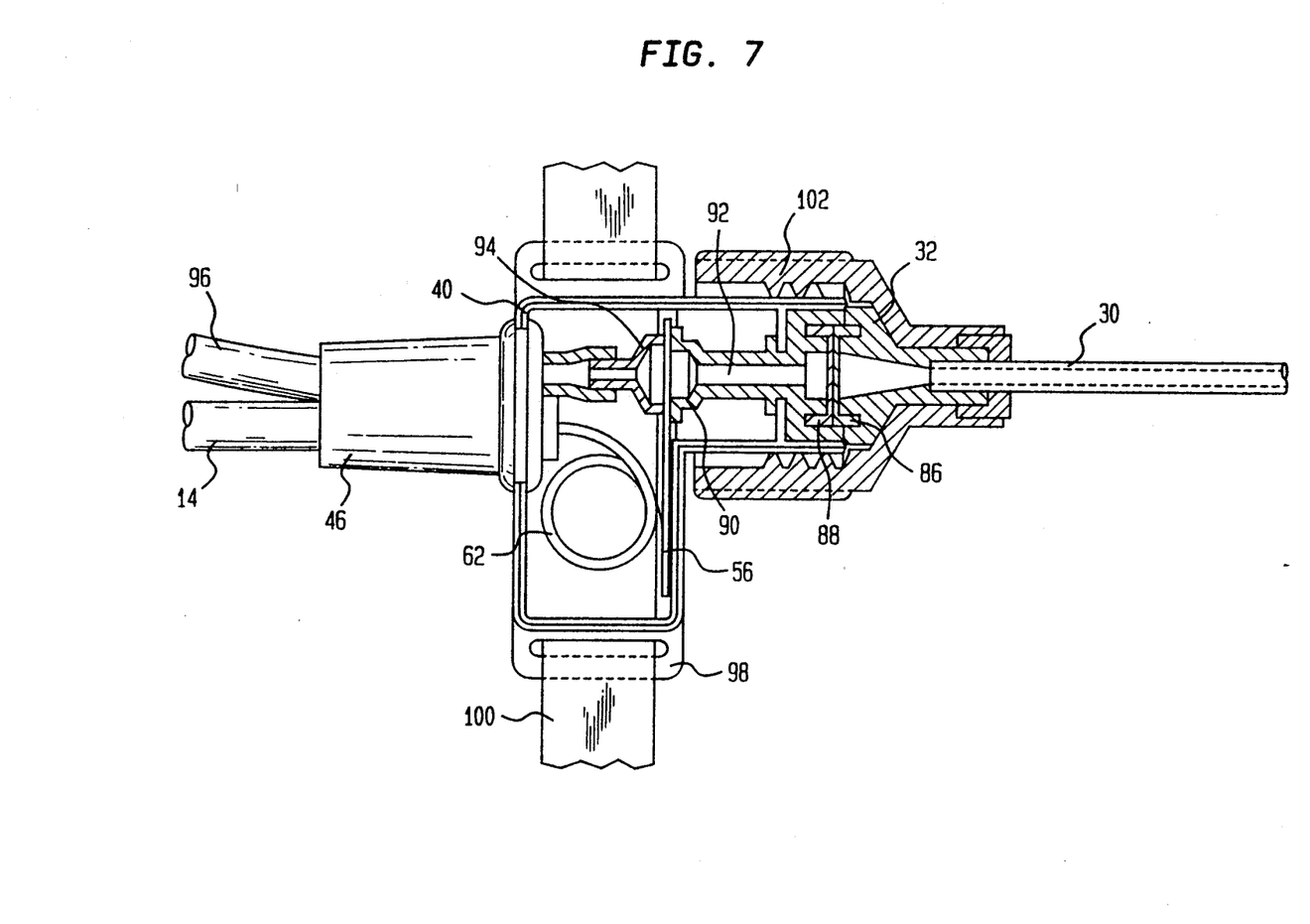
FIG. 7 shows transmission of a pressure signal from the disposable catheter, which is attached to the junction box by the connector, to the sensor, which is housed in the reusable junction box, through a pair of contacting diaphragms.

FIG. 7 illustrates an alternative design for disposable connector 32 which can be attached to reusable junction box 12 containing pressure sensor 56. In this design, which eliminates needle 50, the pressure in lumen 30 of catheter 22 held in connector 32 is transmitted to sensor 56 by a pair of contacting diaphragms: a connector diaphragm 86 and a junction box diaphragm 88. A change in intrauterine pressure is reflected by a change in fluid or air pressure in lumen 30 of catheter 22. That pressure signal deflects adjacent diaphragms 86 and 88 and, in turn, is transmitted to pressure sensor 56.

A diaphragm holder 90 positions junction box diaphragm 88 adjacent to connector diaphragm 86. The intimate contact required between diaphragms 86 and 88 to transmit pressure signals can be assured by a compression sealed connection at the perimeter of diaphragms 86 and 88 and by the placement of liquid at the interface of diaphragms 86 and 88 during joining.

Deflection of diaphragms 86 and 88 transmits a change in pressure in the region 92 between junction box diaphragm 88 and sensor 56. Region 92 may contain either air or liquid as the transmission medium. A sensor vent adapter 94 leads to a sensor vent and calibration tube 96 defining a calibration port for calibrating pressure sensor 56. The pressure change detected by pressure sensor 56 is transmitted through cable 14 to a conventional monitoring device. Pressure sensor 56 is housed within junction box case 40.

System 10 can be affixed to the patient in a number of conventional ways. For example, junction box case 40 may contain a slotted mounting flange 98 which, when a strap 100 is placed through the slot, permits junction box 12 to be attached to the patient. A recessed connection to a post mounted on a foam pad, tape, or other conventional attachment mechanisms are also suitable. Connector 32 may similarly be affixed to the patient. For example, FIGS. 4A and 4B illustrate connector 32 with mounting flange 98. Separate attachment of junction box 12 and connector 32 to the patient is possible and may be desirable when connector 32 is disconnected from junction box 12 for zeroing.

Figure 8:
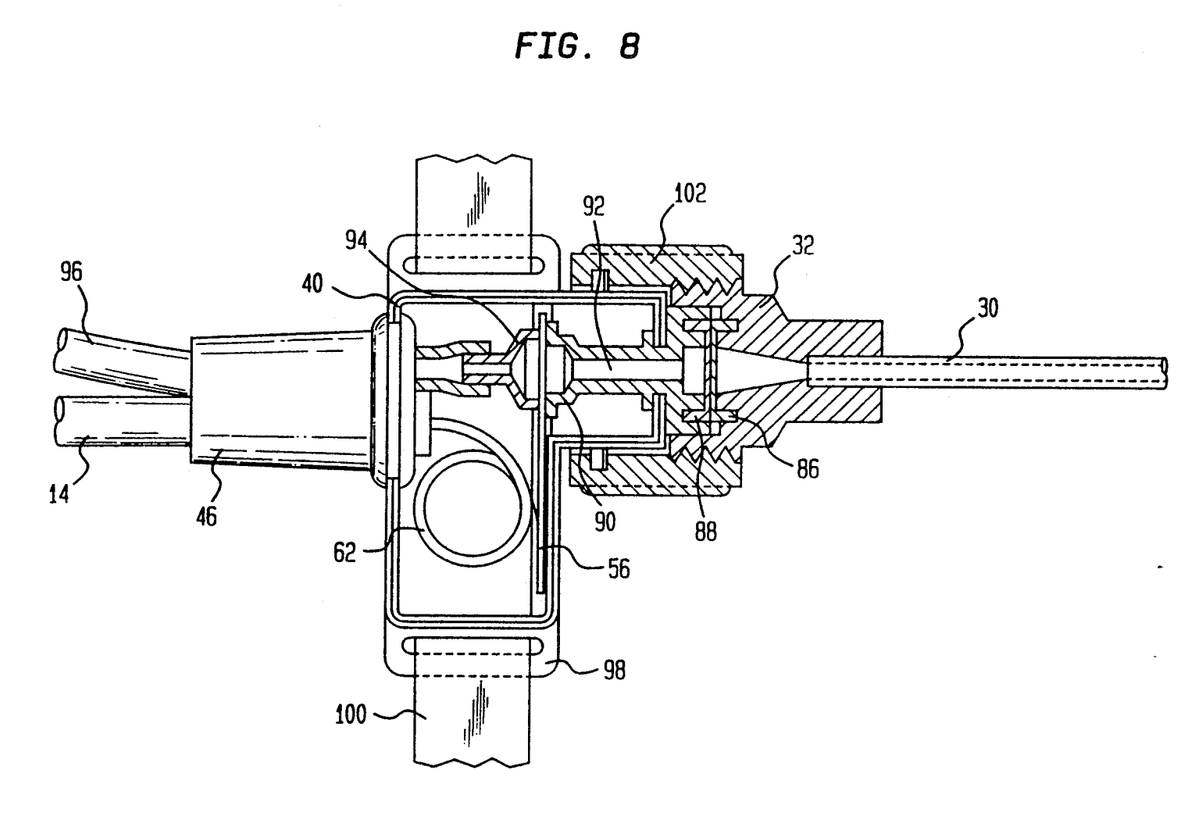
FIG. 8 shows the system of FIG. 7 with the threaded member, used to attach the connector and junction box, placed on the junction box.

System 10 as shown in FIG. 7 may be zeroed by unscrewing the threaded member 102, typically a connector nut provided on connector 32, and separating the diaphragms. Threaded member 102 also can be positioned on junction box 12 as depicted in FIG. 8. The design of FIG. 8 reduces the number of parts in disposable connector 32 and, thus, reduces the cost of the disposable portion of system 10.

Figure 4C:
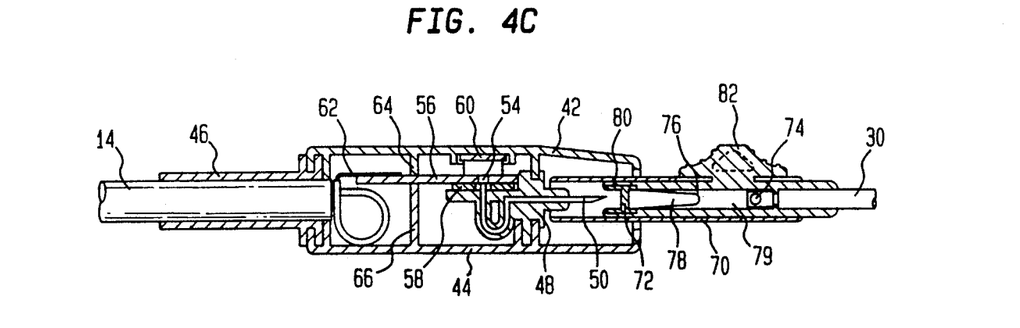
Figure 4D:
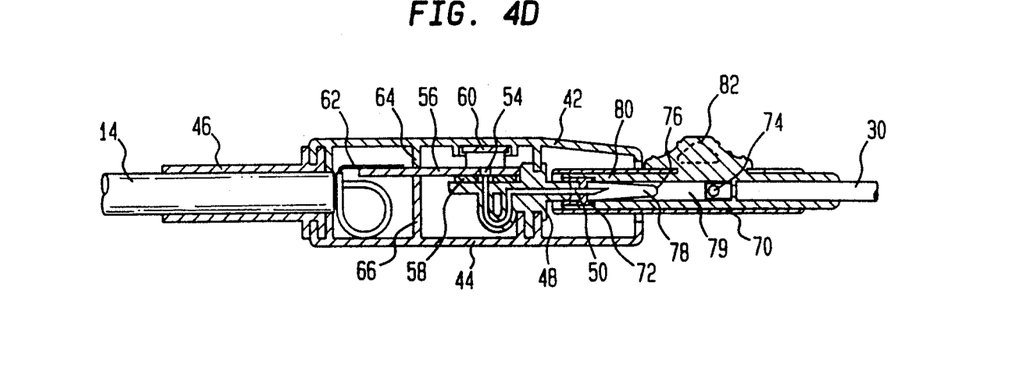

Focusing now on diaphragm 76, as shown in FIGS. 4C, 4D, and 6, diaphragm 76 must be capable of deflecting under fluid pressure from catheter 22. Diaphragm 76 must, with minimum resistance, transmit this pressure signal to sensor 56. Several embodiments of diaphragm 76, each designed to approach a 1-to-1, signal-to-measurement ratio, are shown in FIGS. 9A and 9B; 10A and 10B; 11A, 11B, and 11C; and 12A, 12B, and 12C.

Figure 9A:
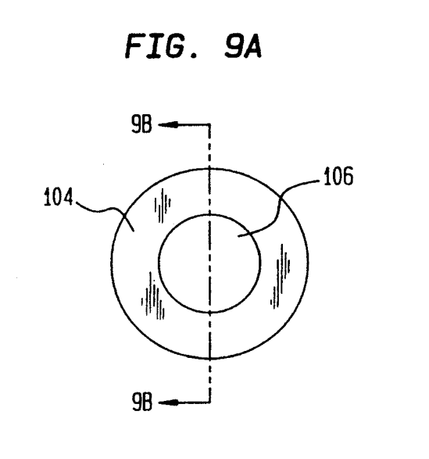
FIGS. 9A and 9B show a conical-shaped diaphragm.
Figure 9B:
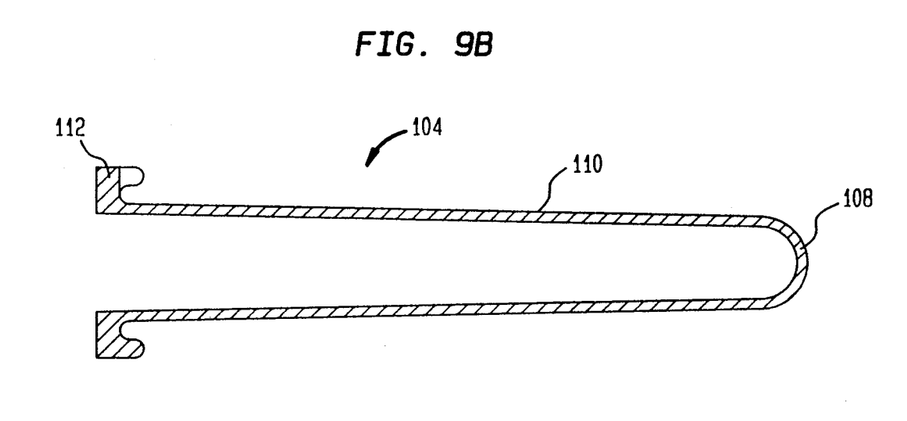

FIG. 9A illustrates the circular end view of alternate diaphragm 104. The central opening 106 of diaphragm 104 has a diameter of about 0.100 inches and the outer diameter of diaphragm 104 is between 0.170 and 0.175 inches. FIG. 9B is a cross-section taken along line 9B—9B of FIG. 9A, showing the slightly tapered, conical shape of diaphragm 104. The radius of the circular tip 108 of diaphragm 104 is about 0.040 inches. Thus, diaphragm 104 tapers about 0.020 inches along its length of about 0.745 inches. The wall 110 of diaphragm 104 is between 0.005 and 0.007 inches thick. A circular flange 112 is provided to attach diaphragm 104 to connector 32. The relatively simple design of diaphragm 104 results in an advantageously low tooling cost.

Figure 10A:
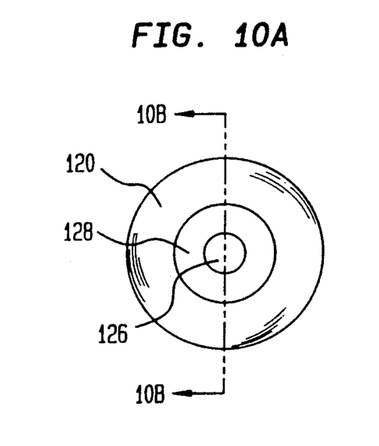
FIGS. 10A and 10B show a bellows-shaped diaphragm.
Figure 10B:
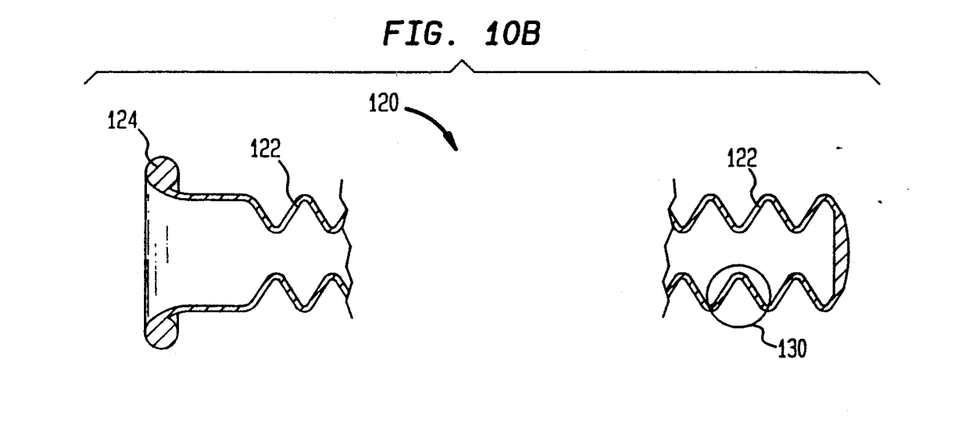

FIG. 10A illustrates the circular end view of another alternative diaphragm 120. FIG. 10B is a cross-section taken along line 10B—10B of FIG. 10A, showing the bellows-shaped wall 122 of diaphragm 120. Wall 122 has a thickness of between 0.004 and 0.006 inches. Rolled ends 124 are provided to attach diaphragm 120 to connector 32. The first central opening 126 of diaphragm 120, defined by the portions of wall 122 which most closely touch, has a diameter of about 0.040 inches. The second central opening 128 of diaphragm 120, defined by the portions of rolled ends 124 which most closely touch, has a diameter of about 0.095 inches. The outer diameter of diaphragm 120 is about 0.170 inches and diaphragm 120 has a length of about 0.700 inches. The number of equal convolutions 130 provided in wall 122 is preferably thirteen, disposed along a length of about 0.600 inches.

Figure 11A:
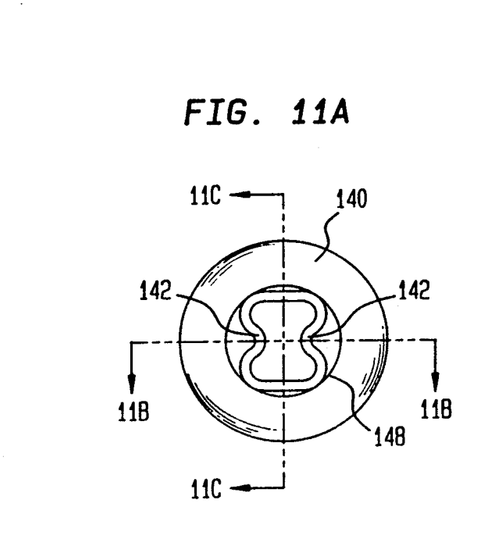
FIGS. 11A, 11B, and 11C show a lobe axial bellows-shaped diaphragm.
Figure 11B:
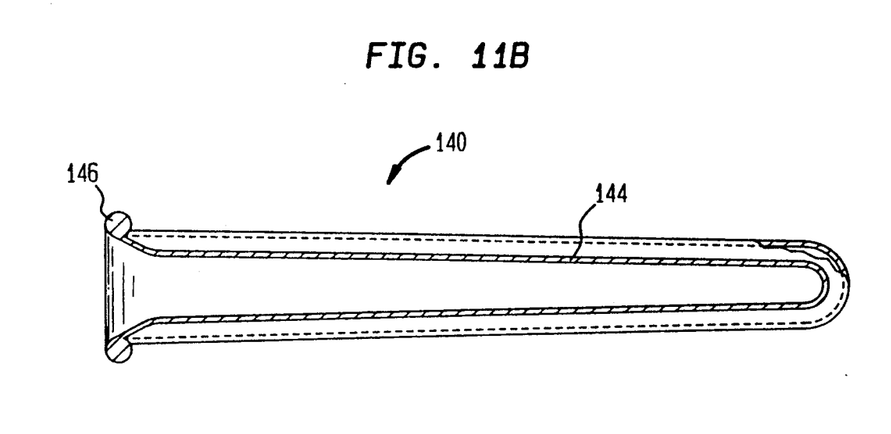
Figure 11C:
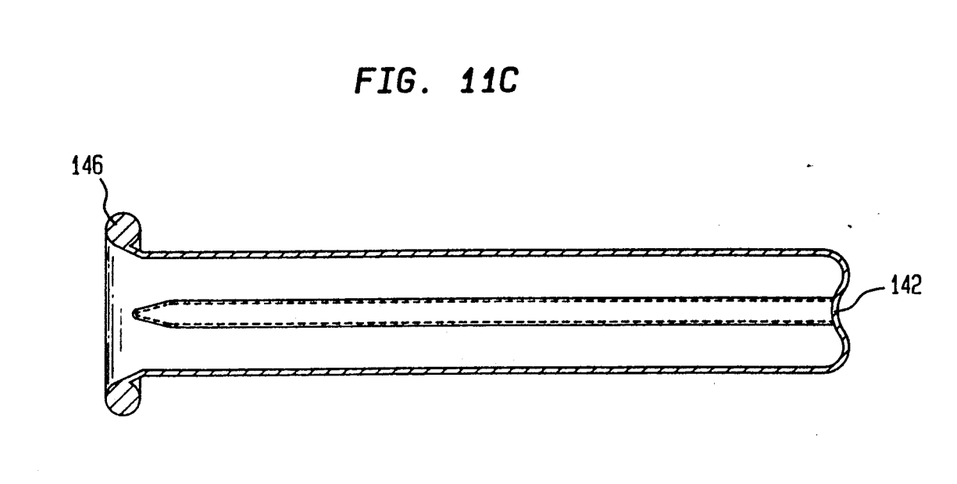

FIG. 11A illustrates the circular end view of yet another alternative diaphragm 140. FIG. 11B is a cross-section taken along line 11B—11B of FIG. 11A; FIG. 11C is a cross-section taken along line 11C-11C of FIG. 11A. As illustrated, diaphragm 140 has two axial lobes 142. Diaphragm 140 might be provided with four or more axial lobes.

Diaphragm 140 has a wall 144 with a thickness of between 0.005 and 0.007 inches. Rolled ends 146 are provided to attach diaphragm 140 to connector 32. The central opening 148 of diaphragm 140, defined by the portions of rolled ends 146 which most closely touch, has a diameter of about 0.100 inches. The outer diameter of diaphragm 140 is about 0.175 inches and diaphragm 140 has a length of about 0.700 inches.

Figure 12A:
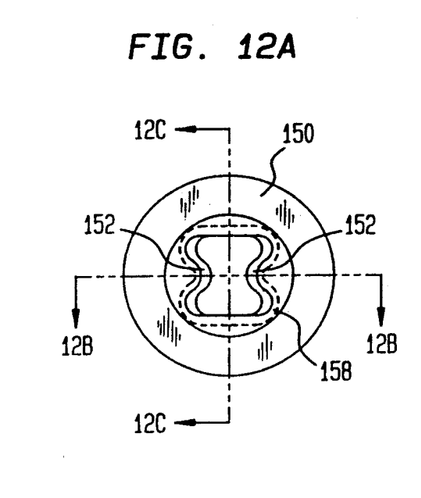
FIGS. 12A, 12B, and 12C show a lobe axial bellows-shaped diaphragm which is larger in size than that of FIGS. 11A, 11B, and 11C.
Figure 12B:
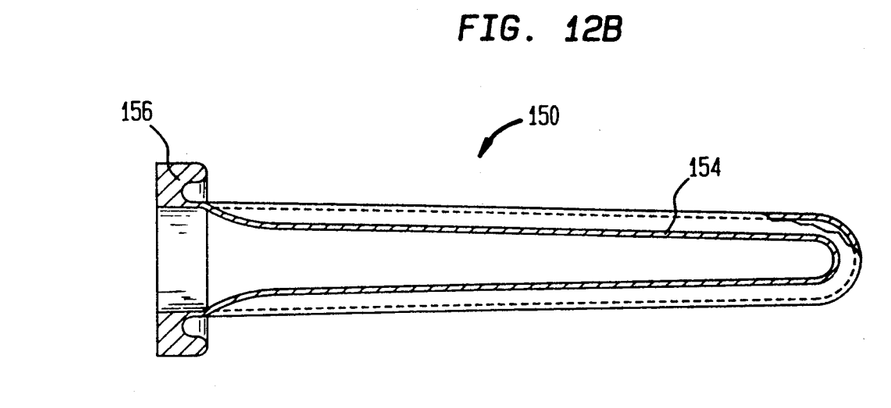
Figure 12C:
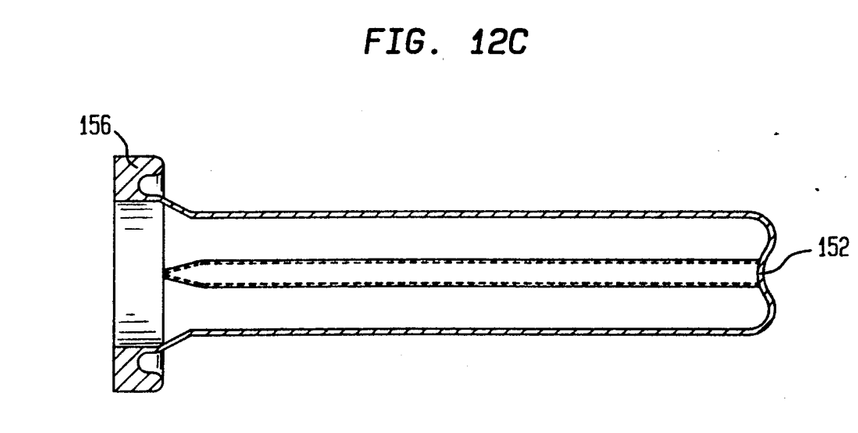

FIGS. 12A, 12B, and 12C illustrate a diaphragm 150 which is similar to, but larger in size than, diaphragm 140 shown in FIGS. 11A, 11B, and 11C. FIG. 12A is the circular end view of diaphragm 150. FIG. 12B is a cross-section taken along line 12B—12B of FIG. 12A; FIG. 12C is a cross section taken along line 12C—12C of FIG. 12A. As illustrated, diaphragm 150 has two axial lobes 152. Diaphragm 150 might be provided with four or more axial lobes.

Diaphragm 150 has a wall 154 with a thickness of between 0.005 and 0.007 inches. Mounting end 156 is provided to attach diaphragm 150 to connector 32. The central opening 158 of diaphragm 150, defined by mounting end 156, has a diameter of about 0.175 inches. The outer diameter of diaphragm 150 is about 0.250 inches and diaphragm 150 has a length of about 0.750 inches.

Because diaphragms 140 and 150 provide the closest 1-to-1, signal-to-measurement ratio, they are the preferred alternative diaphragms.

Diaphragms 104, 120, 140, and 150 are made of an elastomeric material such as rubber or silicone. The material should be radiation resistant. Diaphragms 104, 120, 140, and 150 can be molded by a liquid injection process. That process provides multiple cavities with repeatable performance and avoids damage due to irradiation during sterilization.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. An intrauterine pressure catheter system for monitoring pressure in the uterus of a mother during labor and delivery, said system comprising:
   a disposable catheter including a distal end adapted for insertion in the uterus and having:
   (a) a lumen disposed partially inside and along the length of said catheter including first apertures located at said distal end of said catheter receiving fluid both from, and indicative of pressure changes in, the uterus, and
   (b) a connector mounted on the end of said lumen of said catheter external to the uterus and including an elastomeric plug and a diaphragm, said elastomeric plug and said diaphragm defining an air-filled volume therebetween and said diaphragm communicating the pressure changes indicated by the fluid in said lumen to the air in said air-filled volume while preventing the fluid in said lumen from entering said air-filled volume;
   a reusable junction box with an opening and having:
   (a) a pressure transducer sensor converting physical pressure signals into corresponding electrical signals, and
   (b) a hollow needle communicating directly with said sensor on one end and having a pointed opposite end adapted to pierce said elastomeric plug of said connector and enter said air-filled volume between said elastomeric plug and said diaphragm when said connector is removably inserted into said opening of said junction box, said needle communicating the pressure changes of the air in said air-filled volume to said sensor; and
   a monitor receiving and displaying said electronic signals from said sensor.

2. The intrauterine pressure catheter system of claim 1 wherein said connector has a flexible latch releasably holding said connector in said junction box.

3. The intrauterine pressure catheter system of claim 1 where said catheter has a tube disposed partially inside and along the length of said catheter including second apertures located at said distal end of said catheter injecting fluid into and sampling fluid from the uterus.

4. The intrauterine pressure catheter system of claim 3 wherein said lumen and said tube are completely separate and sealed from each other.

5. The intrauterine pressure catheter system of claim 1 wherein said point of said needle is safely located in said junction box about 0.18 inches from said opening of said junction box and centered within said junction box.

6. The intrauterine pressure catheter system of claim 5 wherein said opening of said junction box has a diameter of about 0.3 inches.

7. The intrauterine pressure catheter system of claim 1 wherein said sensor is resiliently mounted in said junction box between a foam seal and a foam pad restricting movement of said sensor and isolating said sensor from mechanical abuse.

8. The intrauterine pressure catheter system of claim 7 wherein said junction box has a pair of deflection barriers further restricting movement of said sensor.

9. The intrauterine pressure catheter system of claim 1 wherein said junction box has an adhesive seal preventing fluid from entering said junction box in the region of said sensor.

10. The intrauterine pressure catheter system of claim 1 wherein said connector has:
(a) an actuator, and
(b) an actuator sleeve in which said elastomeric plug and said diaphragm of said connector are mounted, said actuator sleeve movable by said actuator between a monitor position, in which said actuator sleeve is fully inserted in said opening of said junction box and said needle point pierces said elastomeric plug and enters said air-filled volume between said elastomeric plug and said diaphragm, and a zero position, in which said actuator sleeve is only partially inserted in said opening of said junction box and said needle point is removed from said elastomeric plug and said air-filled volume and is exposed to atmospheric pressure.

11. The intrauterine pressure catheter system of claim 10 wherein said connector has an anti-return arm positioned on said actuator preventing accidental movement of said actuator and minimizing the force required to move said actuator.

12. The intrauterine pressure catheter system of claim 1 wherein said connector has means for affixing said connector to the mother.

13. The intrauterine pressure catheter system of claim 12 wherein said junction box has means for affixing said junction box to the mother.

14. The intrauterine pressure catheter system of claim 1 wherein one of said junction box and said connector has a threaded member connecting said junction box and said connector.

15. The intrauterine pressure catheter system of claim 1 wherein said connector has a self-sealing fill plug permitting access of a syringe to said tube of said 16. The intrauterine pressure catheter system of claim 1 wherein said diaphragm has a tapered conical configuration.

17. The intrauterine pressure catheter system of claim 1 wherein said diaphragm has a bellows configuration.

18. The intrauterine pressure catheter system of claim 1 wherein said diaphragm has at least two axial lobes.

* * * * *

UNITED STATES PATENT AND TRADEMARK OFFICE
CERTIFICATE OF CORRECTION

PATENT NO. : 5,279,308
DATED : January 18, 1994
INVENTOR(S) : David M. DiSabito et al.

It is certified that error appears in the above-indentified patent and that said Letters Patent is hereby corrected as shown below:

Column 5, line 47, delete "Case" and insert --case--;

Column 6, line 17, delete "TO" and insert --To--;

Column 6, line 38, delete "Of" and insert --of--; and

Column 12, Claim 15, line 22, after "said", second occurrence, insert --catheter.--.

Signed and Sealed this

Twelfth Day of July, 1994

Attest:

BRUCE LEHMAN

*Attesting Officer*     *Commissioner of Patents and Trademarks*